United States Patent
Liu et al.

(10) Patent No.: US 6,293,137 B1
(45) Date of Patent: Sep. 25, 2001

(54) HYDROGEN SENSOR

(75) Inventors: Wen-Chau Liu; Huey-Ing Chen; Hsi-Jen Pan, all of Tainan (TW)

(73) Assignee: National Science Council (TW)

( * ) Notice: Subject to any disclaimer, the term of this patent is extended or adjusted under 35 U.S.C. 154(b) by 0 days.

(21) Appl. No.: 09/564,742

(22) Filed: May 4, 2000

(51) Int. Cl.[7] .............................. G01N 7/00; G01N 27/00
(52) U.S. Cl. .............................................. 73/31.06; 422/98
(58) Field of Search ................................ 73/31.06, 31.01, 73/31.05; 117/103; 204/415, 418; 340/540; 422/88, 98; 438/48, 49

(56) References Cited

PUBLICATIONS

Dutta et al., "Deposition and Characterization on Zinc Oxide Thin Films for Hydrogen Sensor Devices", Materials Science and Engineering B14:31–35, 1992.

Yadava et al., "A Titanium Dioxide–Based MOS Hydrogen Sensor", Solid State Electronics 33:1229–1234, 1990.

*Primary Examiner*—Hezron Williams
*Assistant Examiner*—Jay L Politzer
(74) *Attorney, Agent, or Firm*—Fish & Richardson P.C.

(57) ABSTRACT

In this invention, we propose a high-sensitivity Pd/InP hydrogen sensor. First, a n-type InP semiconductor membrane is grown on a semi-insulating InP substrate. The concentration and thickness of this membrane are $2 \times 10^{17} cm^{-3}$ and 3000 Å, respectively. Then, Pd metal and AuGe alloy are evaporated on the surface of the membrane as the anode and cathode electrodes, respectively. Due to the catalytic performance of Pd metal, the adsorbed hydrogen molecules on the surface of the Pd metal are dissociated into hydrogen atoms. The hydrogen atoms diffuse and pass through the Pd metal and form a dipole layer at the interface between the Pd metal and the n-type InP membrane. This dipole layer will decrease the depletion width of the n-type InP membrane and further lower the metal-semiconductor Schottky barrier height. Therefore, the current-voltage (I–V) characteristics will be modulated after the introduction of hydrogen gas.

12 Claims, 6 Drawing Sheets

Fig. 2a
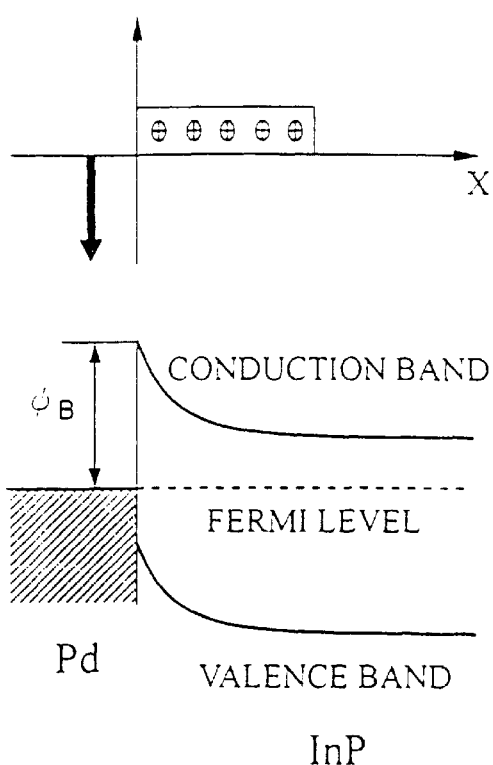
Fig. 2a'
Fig. 2b
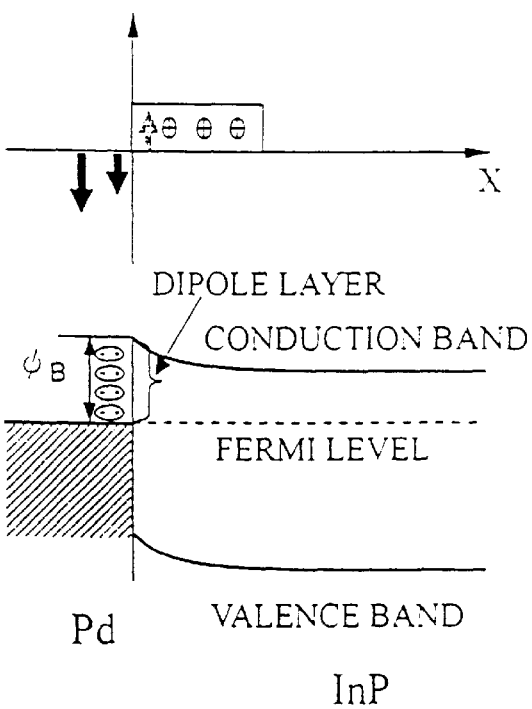
Fig. 2b'

HYDROGEN SENSOR

FIELD OF THE INVENTION

The present invention is related to a highly sensitive Pd/InP hydrogen sensor. In particular, this new Pd/InP hydrogen sensor has advantages of a small size and a simple fabrication process.

BACKGROUND OF THE INVENTION

Due to the technology developments, modern industrial and medical applications use a large quantity of hydrogen as a raw material or other purposes. Hydrogen, however, is a flammable and explosive gas. When the concentration of leakage hydrogen reaches 4.65 vol % or more in air, a hazard of explosion emerges. Therefore, based on the considerations of industrial safety and environmental concern, hydrogen sensors are widely used in factories, laboratories and hospitals in order to accurately monitor the concentration of leakage hydrogen. However, in addition to a large volume and a high production cost, one disadvantage of conventional hydrogen sensors is that most belong to the category of passive elements. The other additional equipment or a conversion circuit is required to perform the analysis or amplification. Therefore, the conventional hydrogen sensors can not become intelligent sensors. As a result, the development of a new and effective hydrogen sensor that is intelligent and of the active type has become an important topic in modern industries.

In recent years, due to the advance of silicon semiconductor technology, much attention has been attracted on the use of a Pd metaloxide-semiconductor (MOS) structure as a semiconductor hydrogen sensor. The reason for using the Pd metal in the hydrogen sensor lies in that Pd has a good catalytic activity and can dissociate the hydrogen molecule adsorbed to the surface into hydrogen atoms. A portion of the hydrogen atoms diffuses through the Pd metal and is adsorbed to the interface between the metal and the oxide layer. These hydrogen atoms, after polarization, cause a change in the Schottky barrier height between the oxide layer and the silicon semiconductor and thus the electrical properties of the device. In the early days, I. Lundstrom proposed a Pd/SiO$_2$/Si MOS field effect transistor structure with a Pd gate [Lundstrom, M. S. Shivaraman, and C. Svensson, J. Appl. Phys., 46, 3876 (1975)]. After the hydrogen being adsorbed to the Pd gate, the altered threshold voltage and terminal capacitance are used as the two bases for the detection of hydrogen. However, the use of a three-terminal device to realize the functions of a two-terminal device not only increases the cost, but also has elevated process difficulties. Furthermore, the quality of the oxide layer will also influence the hydrogen detection capability. In addition to the problem of reliability, the quality of an oxide layer becomes unstable due to the growth of the thin oxide layer is contaminated by the ions or the increase of defects. This results in the surface state pinning of Fermi-level of silicon semiconductor. Therefore, Schottky barrier height is less influenced by the polarized hydrogen atoms and subsequently the hydrogen sensitivity is lower. Many researches focus on how to improve such a problem. For example, A. Dutta et al. [A. Dutta, T. K. Chaudhuri, and S. Basu, Materials Science Engineering, B14, 31 (1992)] used zinc oxide (ZnO) and L. Yadava et al. [L. Yadava, R. Dwivedi, and S. K. Srivastava, Solid-St. Electron., 33, 1229 (1990)] used titanium dioxide (TiO$_2$) to replace the oxide layer of silicon dioxide. On the other hand, the use of a two-terminal type Schottky barrier diode seems to be a more intuitive approach. Without the unstable factors of the oxide layer, the sensitivity of the device to hydrogen has a significant improvement. Therefore, for example, M. C. Steelee et al. [M. C. Steele and B. A. Maciver, Appl. Phys. Lett., 28, 687 (1976)] proposed a Pd/CdS structure, and K. Ito et al. [K. Ito, Surface Sci., 86, 345 (1982)] proposed a Pd/ZnO structure. The using II–VI compound semiconductor as the material is mainly due to the less effect of surface states of II–VI compound semiconductor as compared to the polarized hydrogen atoms.

SUMMARY OF THE INVENTION

A primary objective of the present invention is to provide a highly sensitive hydrogen sensor, which comprises:

a semiconductor substrate;

an n-type semiconductor film formed on said semiconductor substrate; and an anode and a cathode formed on the same surface of said semiconductor film and isolated from each other, wherein a first metal as said anode forms a Schottky contact with said semiconductor film and a second metal as said cathode forms an Ohmic contact with said semiconductor film, wherein a thickness of said first metal and a material of which said first metal is made enable a Schottky barrier height of said Schottky contact to decrease when hydrogen contacts an exposed surface of said first metal.

In a hydrogen sensor according to the present invention, the material and the thickness of said first metal enable hydrogen to be dissociated into hydrogen atoms when the hydrogen comes into contact with the exposed surface of said first metal. Also, said hydrogen atoms diffuse through said first metal, so said Schottky barrier height decreases.

Preferably, said first metal is Pd or Pd alloy, more preferably Pd. Said Pd, preferably, has a thickness of 2000 Angstrom to 5 micron.

In a hydrogen sensor according to the present invention, preferably, said semiconductor substrate is made of a semi-insulating InP material.

In a hydrogen sensor according to the present invention, preferably, said semiconductor film is an n-type III–V Group compound, more preferably, an n-type InP (n-InP). An appropriate doping concentration of said n-InP is of $1\times10^{16}$ to $5\times10^{17}$ cm$^{-3}$, and an appropriate thickness thereof is 1000 Angstrom to 5000 Angstrom.

In a hydrogen sensor according to the present invention, said second metal preferably is an AuGe alloy. Said AuGe alloy preferably has a thickness of 3000 Angstrom to 5 micron.

In a hydrogen sensor according to the present invention, preferably, said anode has a C shape or a C-like shape. Said cathode has a shape corresponding to the shape of said anode such that said cathode is encompassed by said anode. Alternatively, said cathode has a C shape or a C-like shape and said anode has a shape corresponding to the shape of said cathode such that said anode is encompassed by said cathode.

In a Pd/InP hydrogen sensor made according to one of the preferred embodiments of the present invention, a Pd film is used as a catalytic metal to dissociate a hydrogen molecule into hydrogen atoms. The interface between the InP film and the Pd film being capable of adsorbing a large amount of hydrogen atoms is used to obtain a significant linear variation of the diode electrical properties, thereby detecting a low concentration of the hydrogen content.

In order to further elaborate the objectives, characteristics and merits of the present invention, a preferred embodiment together with related figures are disclosed hereinafter.

BRIEF DESCRIPTION OF THE DRAWINGS

FIGS. 2a and 2a' are the charge density distribution and energy band diagrams of the hydrogen sensor shown in FIG. 1, respectively, wherein hydrogen is not detected.

FIGS. 2b and 2b' are the charge density distribution and energy band diagrams of the hydrogen sensor shown in FIG. 1, respectively, wherein hydrogen is detected.

DETAILED DESCRIPTION OF A PREFERRED EMBODIMENT OF THE INVENTION

A highly sensitive Pd/InP hydrogen sensor made according to a preferred embodiment of the present invention comprises: a semi-insulating InP substrate; an n-type InP (n-InP) film on said semi-insulating InP substrate; an Ohmic contact metal layer of AuGe alloy and a Schottky contact metal layer of Pd metal both on said n-InP film, wherein said Ohmic contact metal layer and said Schottky contact metal layer are adjacent to and isolated from each other.

In said highly sensitive Pd/InP hydrogen sensor, said n-InP film is a high quality n-InP film grown on said semi-insulating InP substrate by a metal organic chemical vapor deposition (MOCVD) process. The number of the surface states is greatly reduced by this technique. The Schottky barrier height between metal-semiconductor is therefore closely related to the number of the polarized hydrogen atoms. Furthermore, the InP material has a high hydrogen coverage. This means a very low hydrogen content in air can significantly be detected to alter the Schottky barrier height. Such a property is applicable on a low concentration detection of less than 1%. In terms of the temperature characteristics, the bandgap of the InP material is about 1.35 eV which is larger than silicon; therefore, the InP material has a rather good performances for various temperature. Most importantly, the growth of the InP material and the fabrication process thereof are mature, and have been widely used in the industry of optoelectronic or microwave integrated circuits. The hydrogen sensor of the present invention can thus be integrated with an optoelectronic device into a multi-functional intelligent sensor capable of detecting optoelectronic properties and hydrogen simultaneously. It is believed that the hydrogen sensor of the present invention has a great potential in various applications.

EXAMPLE

Figure 1:
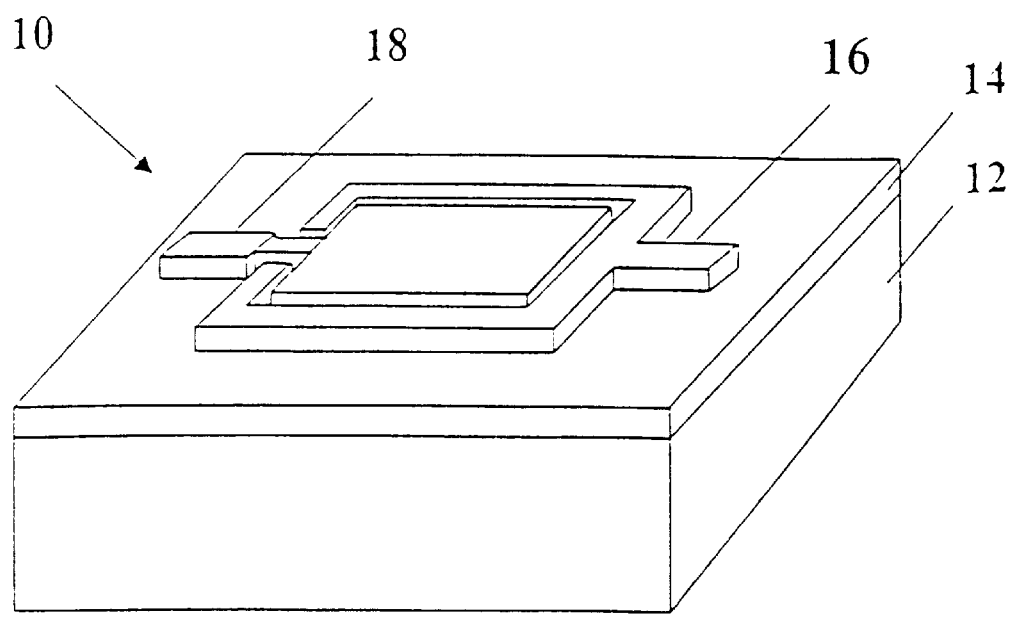
FIG. 1 is an illustrative perspective view of a Pd/InP hydrogen sensor made according to the present invention.

A highly sensitive Pd/InP hydrogen sensor 10 made in this example is shown in FIG. 1. The preparation method includes: preparing a semi-insulating InP substrate 12; growing a high quality n-type InP film 14 on said semi-insulating InP substrate 12 by an metal organic chemical vapor deposition (MOCVD) process, the concentration and the thickness of said n-type InP film 14 being $2 \times 10^{17}$ cm$^{-3}$ and 3000 Å, respectively; and separately evaporating an AuGe Ohmic contact metal layer 16 as a cathode and a Pd metal Schottky contact metal layer 18 as an anode on the surface of said n-type InP film 14 by conventional photolithography and vacuum evaporation techniques.

The charge density distribution and energy band diagrams of the hydrogen sensor in FIG. 1 are shown in FIGS. 2a and 2a' where hydrogen is not detected; and FIGS. 2b and 2b' where hydrogen is detected. Prior to the introduction of hydrogen, the charge distribution of the said sensor at the interface of the Pd metal 18 and the n-type InP film 14 is at equilibrium. A metal-semiconductor Schottky barrier height ($\phi_B$) is thus formed as shown in FIGS. 2a and 2a'. After hydrogen has been introduced, due to the catalytic property of Pd metal 18, the hydrogen molecules will be dissociated into hydrogen atoms when the hydrogen molecules are adsorbed to the surface of the Pd metal 18. Most of the dissociated hydrogen atoms will diffuse through the Pd metal 18 and form a dipole layer at the interface between the Pd metal 18 and the n-type InP film 14. Such a dipole layer will change the equilibrium of original charge distribution and reach a new one. Such a new equilibrium reduces the width of the depletion region of the n-type InP semiconductor thereby reducing the Schottky barrier height ($\phi_B$), as shown in FIGS. 2b and 2b'.

Figure 3:
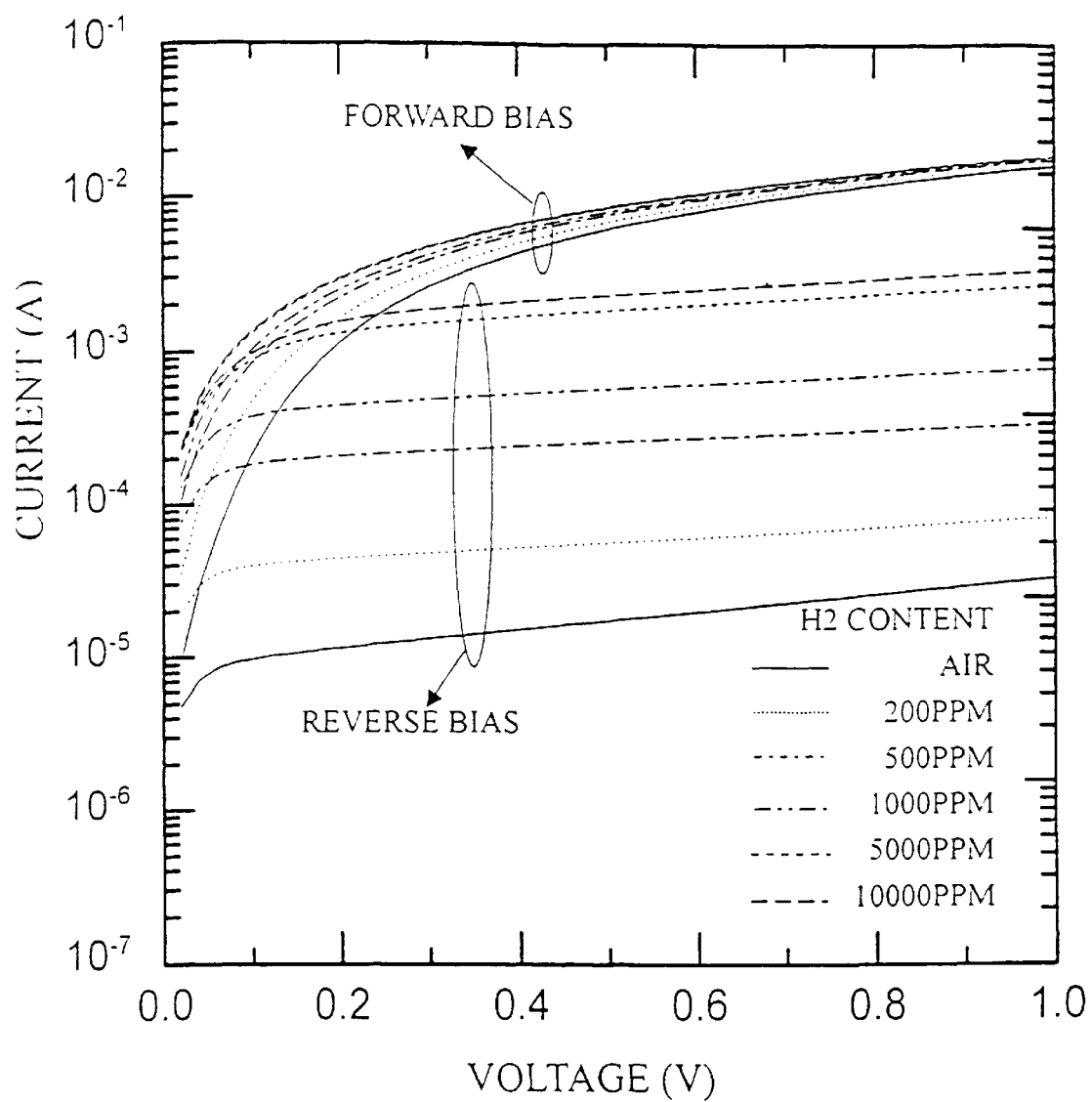
FIG. 3 shows the current-voltage characteristics measured in air and atmospheres which contain 200 ppm, 500 ppm, 1000 ppm, 5000 ppm and 10000 ppm of hydrogen, respectively.

FIG. 3 shows the current-voltage characteristics measured in air and atmospheres which contain 200 ppm, 500 ppm, 1000 ppm, 5000 ppm and 10000 ppm of hydrogen, respectively. In this figure, a forward bias is defined as a positive voltage being applied to the said Schottky contact relative to the said Ohmic contact, on the contrary, a reverse bias for a negative voltage. Due to the Schottky barrier height becomes smaller as the hydrogen content increases, correspondingly the current becomes larger. As it can be seen from FIG. 3, either a forward bias current or a reverse bias current increases as the hydrogen content increases. Moreover, it is apparent that the increase of a reverse current is proportional to the hydrogen content.

Figure 4:
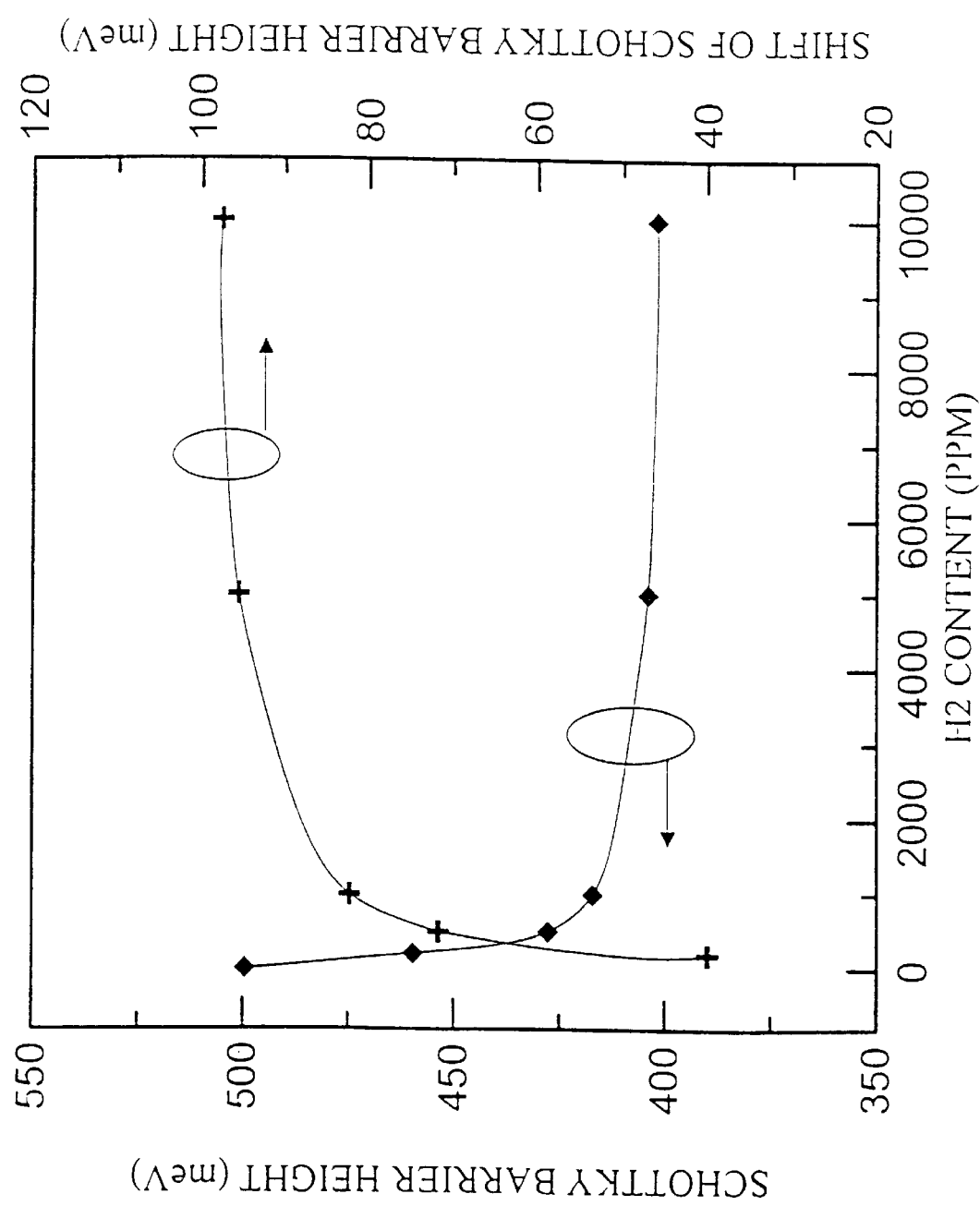
FIG. 4 shows the Schottky barrier height as a function of hydrogen content for the hydrogen sensor of the present invention shown in FIG. 1.

FIG. 4 shows the Schottky barrier height as a function of hydrogen content for the hydrogen sensor of the present invention shown in FIG. 1. The barrier height in air is about 500 meV and reduces gradually along with an increase of the hydrogen content. When the hydrogen content is larger than 0.5%, the barrier height reaches a minimum and the forward current conduction is very close to the Ohmic contact.

Figure 5:
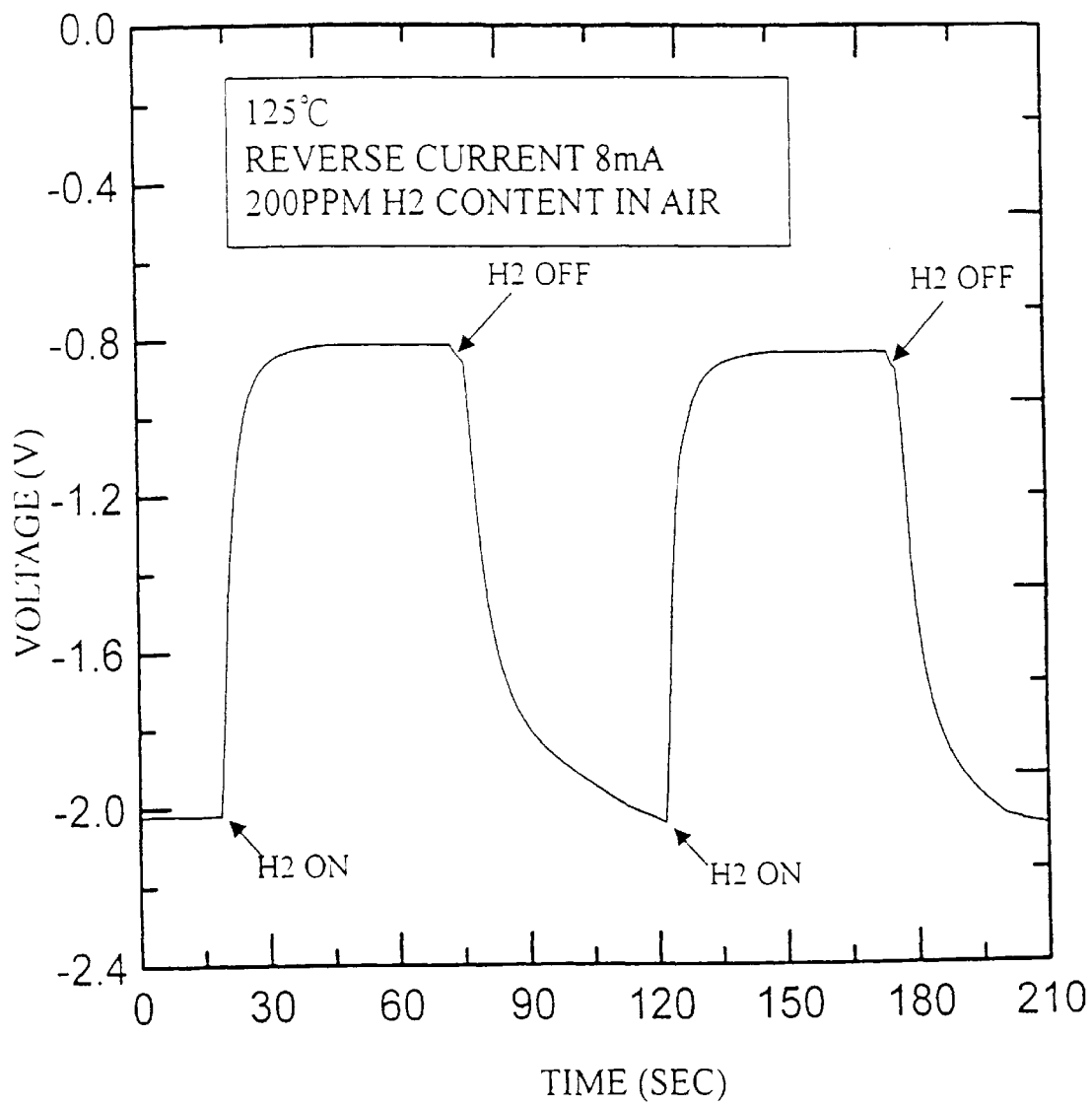
FIG. 5 shows transient responses measured at 125° C. for the hydrogen sensor of the present invention shown in FIG. 1. The gas flow containing 200 ppm of hydrogen was introduced into a test chamber at 500 ml/min. The reverse current of 8 mA was maintained between the two electrodes of the Schottky contact metal layer 18 and the Ohmic contact metal layer 16.

FIG. 5 shows transient responses measured at 125° C. for the hydrogen sensor of the present invention shown in FIG. 1. The gas flow containing 200 ppm of hydrogen was introduced into the test chamber at a flow rate of 500 ml/min. The reverse current of 8 mA was maintained. Due to the dipole layer formed by the dissociated hydrogen atoms, the reverse current increases. Correspondingly, the voltage between the two electrodes decreases for about 1.2 V. On the other hand, when the introduction of hydrogen was turned off, the sensor was exposed in an air. Therefore, the hydrogen atoms are desorbed from the surface of the Pd metal by recombining into hydrogen molecules or water molecules with oxygen. This results in the recovery of the voltage between the two electrodes. We define the reactive time and recovery time as the times are required to reach 90% and 10% of their steady values, respectively. It can be seen from FIG. 5 that the reactive time of the sensor is about 5 seconds and the recovery time is about 12 seconds Furthermore, a second cycle of the transient voltage response was obtained by repeating the first one. A comparison of the two cycles indicates a high reproducibility of the results.

Figure 6:
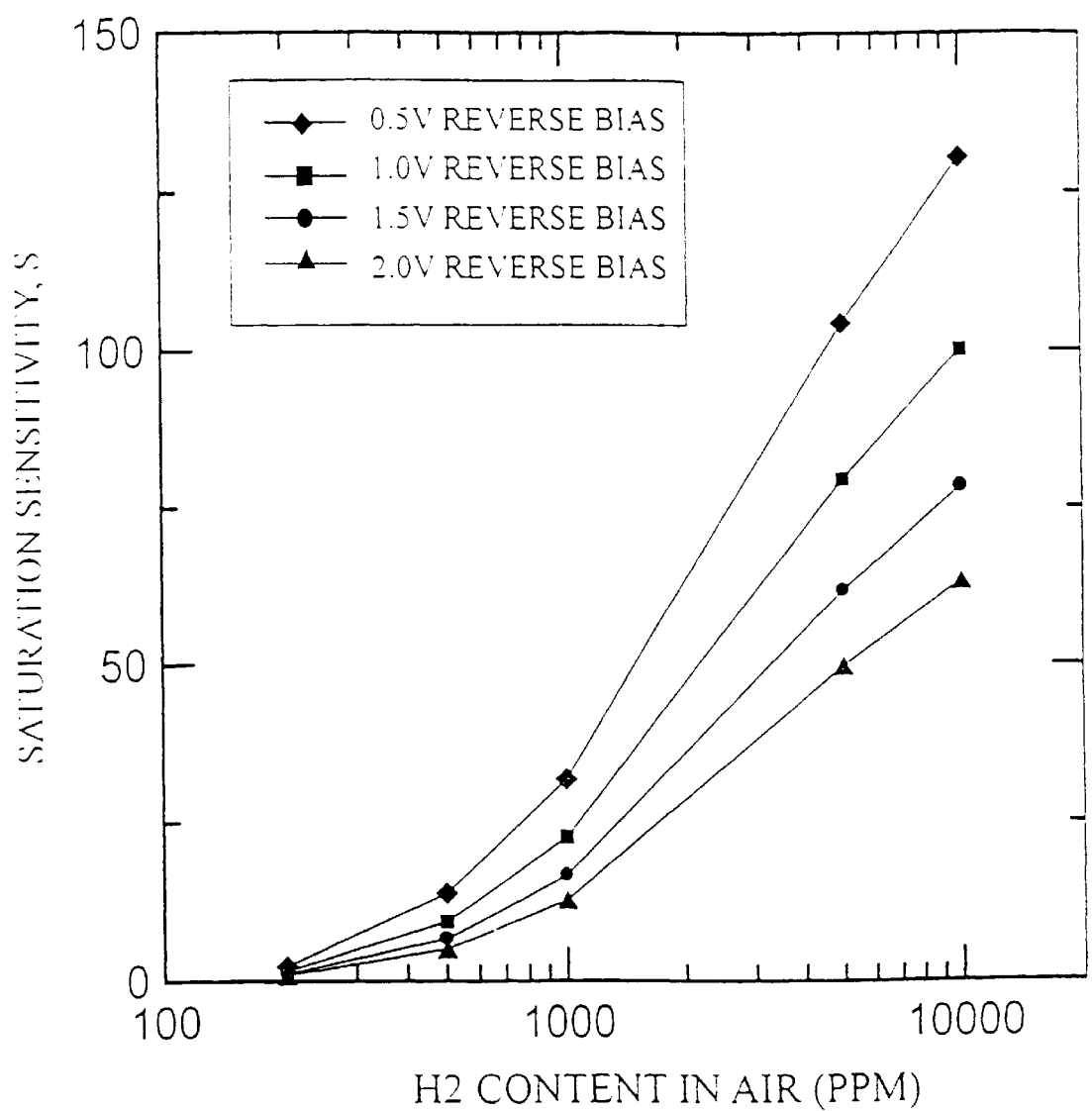
FIG. 6 shows the saturation sensitivity as a function of hydrogen content for the hydrogen sensor of the present invention shown in FIG. 1 under various reverse voltages of 0.5 V (black diamond), 1.0 V (black square), 1.5 V (black round dot) and 2.0 V (black triangle), respectively.

FIG. 6 shows the saturation sensitivity as a function of hydrogen content for the hydrogen sensor of the present invention shown in FIG. 1. The saturation sensitivity, S, is defined as the ratio of the current variation under a constant reverse voltage to the reference current, $(I_{H_2}-I_{air})/I_{air}$. The results in FIG. 6 clearly show that the sensitivity increases monotonically along with the increase of the hydrogen content. At a reverse bias of 0.5 V, a saturation sensitivity of the hydrogen sensor can reach up to 130 in the atmosphere containing 1% hydrogen. The saturation sensitivity can reach 2 even in the atmosphere containing 200 ppm hydrogen.

Based on the above-mentioned disclosure, a hydrogen sensor according to the present invention not only has advantages of a small size, a simple fabrication process and a high capability of being integrated, but shows high linearity, high response time, high reproducibility and high sensitivity compared to a conventional hydrogen sensor.

Even though the present invention is disclosed through a preferred embodiment, the above-mentioned disclosure is not restrictive on the present invention. Any person skilled in the art can make various alterations and modifications without departure from the spirit and scope of the present invention. Therefore, the scope of the present invention is only limited by the claims appended hereinafter.

What is claimed is:

1. A hydrogen sensor comprising:

a semiconductor substrate made of a semi-insulating InP material;

a semiconductor film made of an n-type III–V Group compound material formed on said semiconductor substrate; and an anode and a cathode formed on a same surface of the said semiconductor film and isolated from each other, wherein a first metal as said anode forms a Schottky contact with said semiconductor film and a second metal as said cathode forms an Ohmic contact with said semiconductor film, wherein a thickness of said first metal and a material of which said first metal is made enable a Schottky barrier height of said Schottky contact to decrease when hydrogen contacts an exposed surface of said first metal.

2. The hydrogen sensor according to claim 1, wherein the material and the thickness of said first metal enable hydrogen to be dissociated into hydrogen atoms when the hydrogen is adsorbed with the exposed surface of said first metal, and said hydrogen atoms diffuse through said first metal, so that said Schottky barrier height decreases.

3. The hydrogen sensor according to claim 1, wherein said semiconductor film is n-type InP.

4. The hydrogen sensor according to claim 3, wherein said n-type InP has a doping concentration of $1\times10^{16}$ to $5\times10^{17}$ $cm^{-3}$.

5. The hydrogen sensor according to claim 3, wherein said n-type InP has a thickness of 1000 Angstrom to 5000 Angstrom.

6. The hydrogen sensor according to claim 1, wherein said first metal is Pd or Pd alloy.

7. The hydrogen sensor according to claim 6, wherein said first metal is Pd.

8. The hydrogen sensor according to claim 7, wherein said Pd has a thickness of 2000 Angstrom to 5 micron.

9. The hydrogen sensor according to claim 1, wherein said second metal is an alloy of AuGe.

10. The hydrogen sensor according to claim 9, wherein said alloy of AuGe has a thickness of 3000 Angstrom to 5 micron.

11. The hydrogen sensor according to claim 1, wherein said anode has a C shape or a C-like shape, and said cathode has a shape corresponding to that of said anode, so that said cathode is encompassed by said anode.

12. The hydrogen sensor according to claim 1, wherein said cathode has a C shape or a C-like shape, and said anode has a shape corresponding to that of said cathode, so that said anode is encompassed by said cathode.

* * * * *